(12) United States Patent
Blasse et al.

(10) Patent No.: US 10,849,767 B1
(45) Date of Patent: Dec. 1, 2020

(54) ORTHOTIC GRIPPERS

(71) Applicants: Catherine Marie Blasse, Clearwater, FL (US); Daniel Stewart Miller, Palm Harbor, FL (US); Amber Lynn Gatto, Tampa, FL (US)

(72) Inventors: Catherine Marie Blasse, Clearwater, FL (US); Daniel Stewart Miller, Palm Harbor, FL (US); Amber Lynn Gatto, Tampa, FL (US)

(73) Assignee: University of South Florida, Tampa, FL (US)

( * ) Notice: Subject to any disclaimer, the term of this patent is extended or adjusted under 35 U.S.C. 154(b) by 276 days.

(21) Appl. No.: 15/636,919

(22) Filed: Jun. 29, 2017

Related U.S. Application Data

(60) Provisional application No. 62/356,200, filed on Jun. 29, 2016.

(51) Int. Cl.
  *A61F 5/01* (2006.01)
  *A61F 2/58* (2006.01)
  *A61F 5/058* (2006.01)

(52) U.S. Cl.
  CPC .......... *A61F 2/583* (2013.01); *A61F 5/05866* (2013.01); *A61F 5/013* (2013.01)

(58) Field of Classification Search
  CPC .. A61H 1/0274; A61H 1/0286; A61H 1/0288; A61F 2/583; A61F 5/05866; A61F 5/013; A61F 2002/6872; A61F 2/70; A61F 2/72; G01D 5/35345
  See application file for complete search history.

(56) References Cited

U.S. PATENT DOCUMENTS

| | | | |
|---|---|---|---|
| 5,865,770 A | 2/1999 | Schectman | |
| 8,026,414 B2 | 9/2011 | Kim et al. | |
| 8,255,079 B2 | 8/2012 | Linn et al. | |
| 2008/0071386 A1* | 3/2008 | McBean | A61F 5/0127 623/25 |
| 2012/0059291 A1* | 3/2012 | Nguyen | A61H 1/0288 601/40 |
| 2015/0148728 A1* | 5/2015 | Sallum | A61F 5/10 602/22 |
| 2016/0101309 A1* | 4/2016 | Schreiber | A61F 5/0127 482/124 |

OTHER PUBLICATIONS https://web.wpi.edu/Pubs/E-project/Available/E-project-042513-135953/unrestricted/Design_of_a_Powered_Hand_Orthosis_MQP_Report.pdf (Year: 2013).*

(Continued)

*Primary Examiner* — Brian A Dukert
*Assistant Examiner* — Rebecca Lynee Zimmerman
(74) *Attorney, Agent, or Firm* — Thomas | Horstemeyer, LLP

(57) ABSTRACT

In one embodiment, an orthotic gripper includes a flex sensor configured to detect flexion and extension of a wrist of a user of the gripper, and a gripping mechanism comprising a thumb link configured to attach to a thumb of the user and a finger link pivotally connected to the thumb link and configured to attach to one or more fingers of the user, the gripping mechanism being configured to move the finger link toward the thumb link when the flex sensor detects flexion of the wrist and to move the finger link away from the thumb link when the flex sensor detects extension of the wrist.

17 Claims, 4 Drawing Sheets

(56) References Cited

OTHER PUBLICATIONS

King, et al, "A wrist extension operated lateral key grip orthosis for people with tetraplegia", ISSN, IOS Press, 2009.

Kang, et al, "Biomechanical evaluation of write-driven flexor hinge orthosis in persons with spinal cord injury", JRRD, vol. 50, No. 8, 2013.

Thorsen, et al., "A noninvasive neuroprosthesis augments hand grasp force in individuals with cervical spinal cord injury: The functional and therapeutic effects", Hindawi Publishing Corporation, vol. 213, 2013.

Simpson, L. A., Eng, J. J., Hsieh, J. T., & Wolfe and the Spinal Cord Injury Rehabilitation Evidence (SCIRE) Research Team, D. L. (2012). The health and life priorities of individuals with spinal cord injury: a systematic review. Journal of neurotrauma, 29(8), 1548-1555.

Di Rienzo, F., Guillot, A., Mateo, S., Daligault, S., Delpuech, C., Rode, G., & Collet, C. (2015). Neuroplasticity of imagined wrist actions after spinal cord injury: a pilot study. Experimental brain research, 233(1), 291-302.

Price, G. Achieving Tenodesis Grasp, www.otcats.com, Sep. 2004.

NSC SC Spinal Cord Injury (SCI) Facts and Figures at a Glance, 2016—SCI Data Sheet.

Kalsi-Ryan, et al., "The graded redefined assessment of strength sensibility and prehension: reliability and validity", Thomas Jefferson University, Dept of Physical Therapy Faculty Papers, Mar. 20, 2012.

Leon, et al., "Technical evaluation of and clinical experiences with the SCRIPT passive wrist and hand orthosis", ResearchGate, conference paper, Jun. 2014.

Rudhe, et al, "Reliability of movement workspace measurements in a passive arm orthosis used in spinal cord injury rehabilitation", Journal of Neuroengineering and Rehabilitation, 2012.

* cited by examiner

ORTHOTIC GRIPPERS

CROSS-REFERENCE TO RELATED APPLICATION

This application claims priority to U.S. Provisional Application Ser. No. 62/356,200, filed Jun. 29, 2016, which is hereby incorporated by reference herein in its entirety.

BACKGROUND

When people sustain an injury to the spinal cord at the cervical level, and specifically to the areas of the C-5 to C-7 vertebrae, they lose all of the muscle and motor function in their lower body and most of the muscle and motor function in their upper body. In most cases, such persons will still have the ability to move their arms at the joints of the shoulder, elbow, and wrist. Unfortunately, they normally lose the acute dexterity of theirs hands and fingers. Not only will these individuals live the rest of the their lives in a wheelchair, but many activities of daily living, such as picking up objects and being able to grasp things, becomes a great challenge. This typically means that such individuals must pick up objects by pinching them between both of their wrists. This results in a weaker grasp of the objects and an inability to grasp objects that they would otherwise be able to grip with their hands if they had greater control over them.

In view of the limitations described above, it would be desirable to have an apparatus that assists individuals with impaired function of their upper extremities to grasp objects with their hands.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have an apparatus that assists individuals with impaired function of their upper extremities to grasp objects with their hands. Disclosed herein are embodiments of an orthotic gripper that serves this purpose. In some embodiments, the orthotic gripper comprises a gripping mechanism that attaches to the user's hand and a flex sensor that is associated with the user's wrist. When the user flexes his or her wrist, the gripping mechanism is activated to close the user's hand so that an object can be gripped. When the user extends his or her wrist, the gripping mechanism is activated to open so that a gripped object can be released. In some embodiments, the gripping mechanism and the flex sensor are integrated with a support sleeve that can be worn over the wrist and hand.

In the following disclosure, various specific embodiments are described. It is to be understood that those embodiments are example implementations of the disclosed inventions and that alternative embodiments are possible. All such embodiments are intended to fall within the scope of this disclosure.

Figure 1:
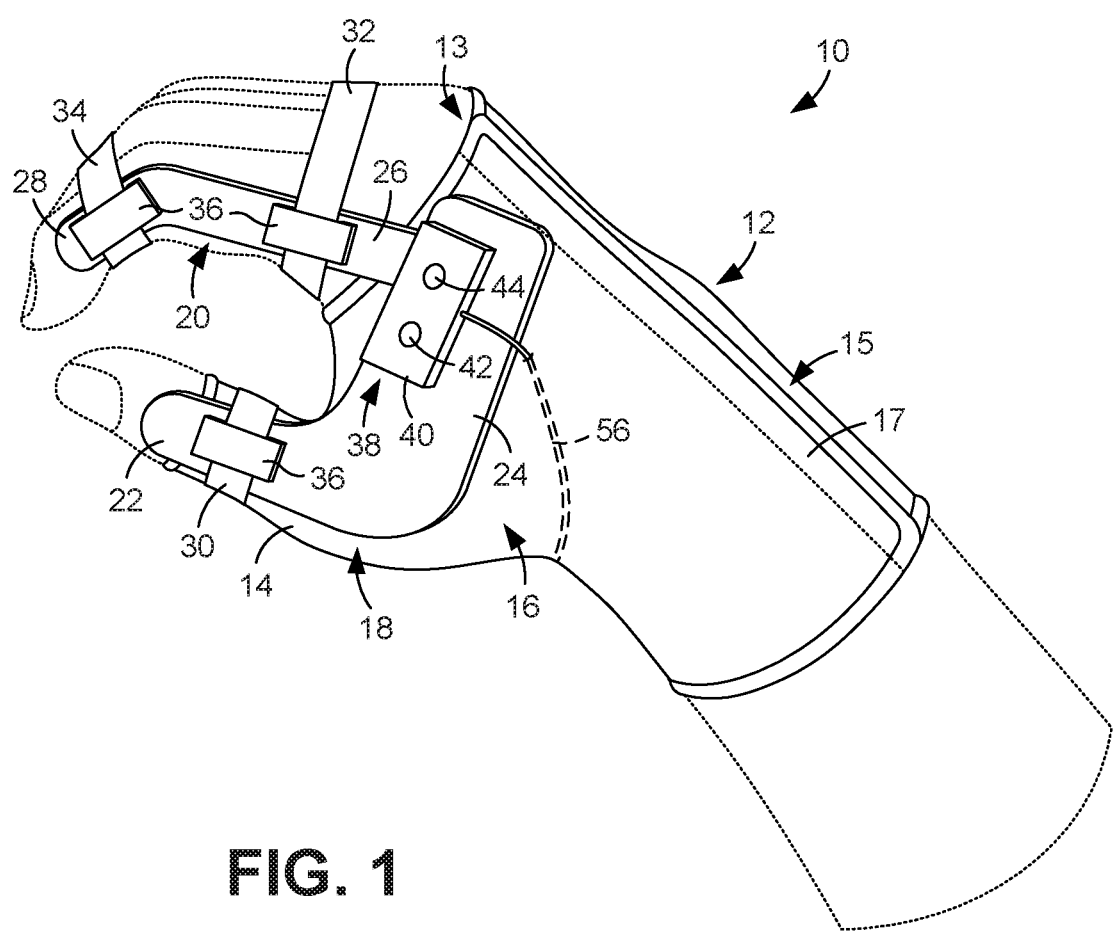
FIG. 1 is a perspective top view of an embodiment of an orthotic gripper shown attached to a user's wrist and hand.
Figure 2:
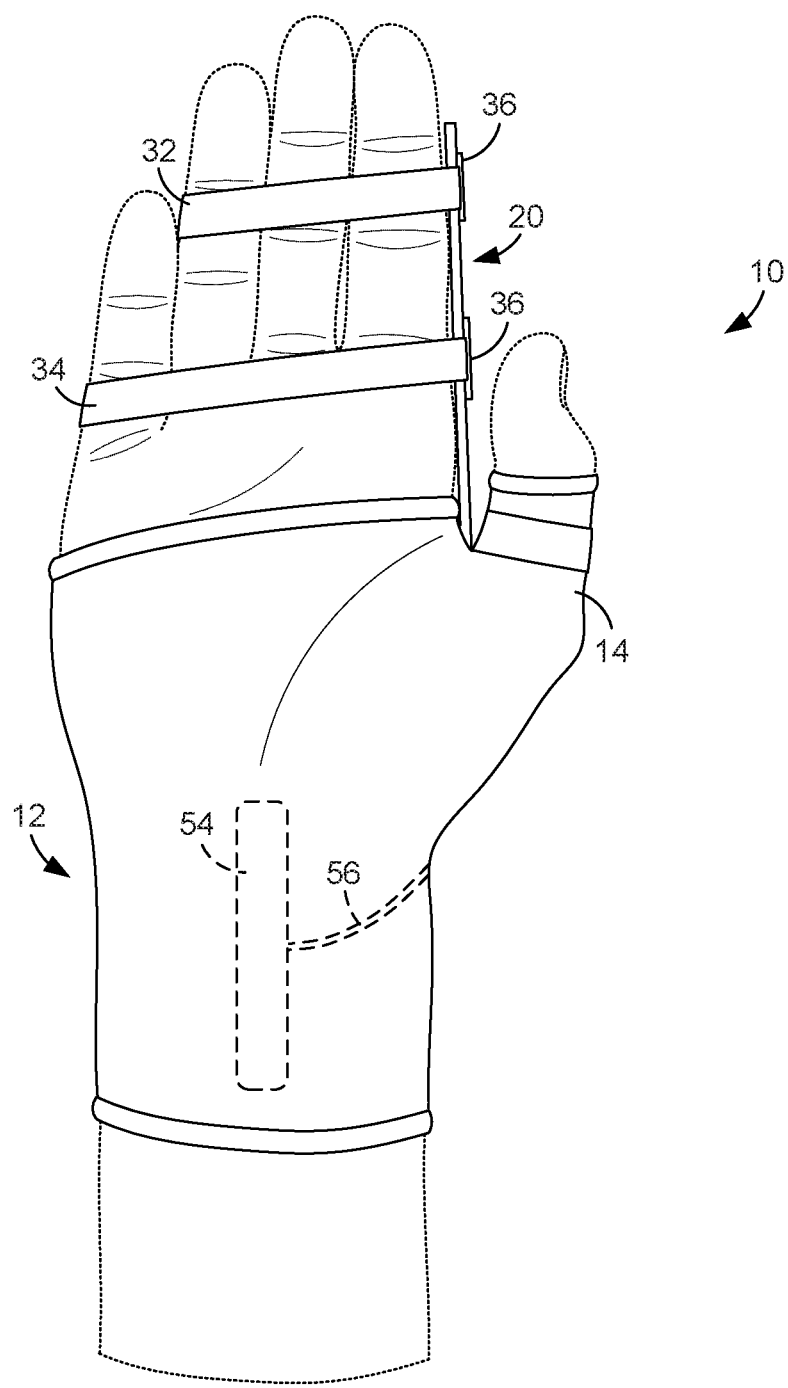
FIG. 2 is a bottom view of the orthotic gripper of FIG. 1.

FIGS. 1 and 2 illustrate an embodiment of an orthotic gripper 10 configured to assist a user with grasping objects. As indicated in these figures, the particular orthotic gripper 10 shown in the drawings is configured for use with the right wrist and hand. Although such an embodiment is illustrated, it will be appreciated that a similar orthotic gripper can be constructed for use with the left wrist and hand.

As shown in FIGS. 1 and 2, the orthotic gripper 10 comprises a support sleeve 12 that is configured to wrap around the user's wrist and hand. The sleeve 12 is generally tubular and generally extends from a point a few inches proximal of the wrist to the knuckles (metacarpophalangeal joints) of the fingers. In the illustrated embodiment, the sleeve 12 includes a finger opening 13 through which the fingers can pass and a thumb sheath 14 that is configured to wrap around the base of the thumb but leave the tip of the thumb exposed. By way of example, the thumb sheath 14 can extend to the distal interphalangeal joint of the thumb. The sleeve 12 can have other configurations in other embodiments. For example, the sleeve 12 can include finger sheaths that cover the bases of the fingers but leave the tips of the fingers exposed (e.g., extend to the distal interphalangeal joints of the fingers). As another example, the sleeve 12 can omit the thumb sheath 14. Irrespective of its particular configuration, the sleeve 12 is made of a flexible material so that it can conform to the contours of the user's wrist and hand. In some embodiments, the flexible material comprises a fabric material that includes natural and/or synthetic fibers. In addition to being flexible, the sleeve 12 can also be elastic so that it snuggly wraps around the wrist and hand. In such cases, the flexible material may be an elastic material, such as spandex.

As shown in FIG. 1, the support sleeve 12 can comprise a seam 15 on its top side that extends along the length of the sleeve from its proximal end to its distal end. In such a case, the top sleeve 12 can be split open along the seam 15 such that the hand and wrist can be "dropped" into the sleeve instead of slid through its proximal end, which makes donning the orthotic gripper 10 easier. The seam 15 can include a releasable closure 17 that can hold the sleeve 12 closed when the gripper 10 is being worn. In some embodiments, the closure 17 comprises hook-and-loop fastening elements.

Provided on the top side of the support sleeve 12 is a gripping mechanism 16 that is configured to assist the user of the orthotic gripper 10 to grasp objects with the hand. In the illustrated embodiment, the gripping mechanism 16 comprises first and second links 18 and 20 that are pivotally connected to each other. The first link 18 is a thumb link that is configured to attach to the user's thumb and the second link 20 is a finger link that is configured to attach to at least the user's index finger. Each link 18, 20 is unitarily formed from a thin piece of rigid, lightweight material. For example, the links 18, 20 can be made of a lightweight metal, such as aluminum or titanium, or a rigid polymeric material. In some embodiments, the links 18, 20 can be made of a composite material, such as fiberglass or carbon fiber.

As shown in FIG. 1, the thumb link 18 is generally L-shaped and includes a thumb portion 22 that extends along a portion of the thumb and a hand portion 24 that overlies a portion of the hand. In some embodiments, the thumb link 18 can be attached to the support sleeve 12 with mechanical or adhesive means such that it remains in this position on the gripping mechanism 16. As depicted in FIG. 1, the thumb portion 22 extends to a point near the distal interphalangeal joint of the thumb and the hand portion 24 overlies a triangular region on the dorsal side of the hand that is defined by the metacarpals of the thumb and index finger.

The finger link 20 is also generally L-shaped and includes a proximal portion 26 and a distal portion 28. As shown in FIG. 1, the finger link 20 extends along the outer lateral side of the index finger facing the thumb with the proximal portion 26 extending along the proximal phalange and the distal portion 28 extending along the middle phalange.

With further reference to FIG. 1, the thumb link 18 and the finger link 20 can be releasably attached to the thumb and at least the index finger, respectively, with a flexible thumb strap 30 and flexible finger straps 32 and 34. As shown in FIG. 1, the thumb strap 30 is positioned along the thumb portion 22 of the thumb link 18 at a location at which it is configured to wrap around the proximal phalange of the thumb. As shown most clearly in FIG. 2, a proximal finger strap 32 is positioned along the proximal portion 26 of the finger link 20 at a location at which it is configured to wrap around the proximal phalanges of each finger, and a distal finger strap 34 is positioned along the distal portion 28 of the finger link 20 at a location at which it is configured to wrap around the middle phalanges of the index, middle, and ring fingers. Like the support sleeve 12, the straps 30-34 can be made of a flexible material that, in some embodiments, is elastic. The straps 30-34 can either comprise endless bands or can have open ends and closure means, such as hook-and-loop fastening elements. As shown in FIG. 1, the straps 30-34 can attach to the thumb and finger links 18, 20 with attachment elements 36. In the illustrated embodiment, a first attachment element 36 is provided on the thumb portion 22 of the thumb link 18, a second attachment element 36 is provided on the proximal portion 26 of the finger link 20, and a third attachment element 36 is provided on the distal portion 28 of the finger link. These attachment elements 36 can comprise flat loops through which the straps 30-34 can be passed.

Although the orthotic gripper 10 is shown and has been described as having thumb and finger straps, it is noted that, in other embodiments, it is possible to omit such straps. For example, in cases in which the support sleeve 12 includes sheaths for the thumb and/or the fingers, it is possible to attach the thumb and/or finger links 18, 20 to the sheaths in a manner in which the straps are not necessary.

With reference again to FIG. 1, mounted to the hand portion 24 of the thumb link 18 is an actuation device 38 of the gripping mechanism 16 that is configured to actuate the mechanism in response to sensed wrist movement. The actuation device 38 comprises an outer housing 40 that contains various electrical components. Integrated into the housing 40 in the illustrated embodiment are a control button 42 and an indicator light 44. The control button 42 can be used to activate and deactivate the gripping mechanism 16. These two states, as well as other states of the mechanism 16, can be identified to the user with the indicator light 44, which can comprise a light-emitting diode.

Figure 3:
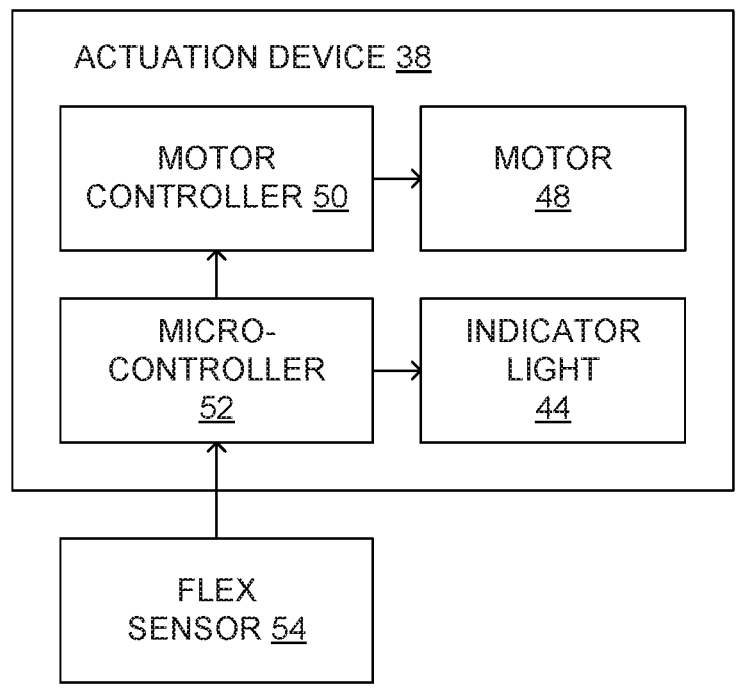
FIG. 3 is a block diagram that identifies electrical components that can be included in an orthotic gripper such as that shown in FIG. 1.
Figure 4:
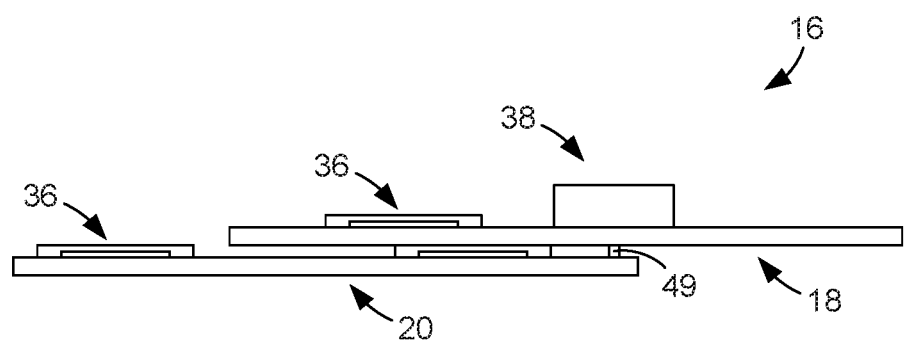
FIG. 4 is a side view of a gripping mechanism shown in FIG. 1.

FIG. 3 identifies the primary components of the actuation device 38. As indicated in this figure, these components include a motor 48, a motor controller 50, a microcontroller 52, and the indicator light 44. The motor 48 includes a shaft (49, FIG. 4) to which the finger link 20 is mounted. When the motor 48 is operated in either the forward or rearward direction so as to rotate the shaft in the forward or rearward angular directions, the finger link 20 is rotated relative to the thumb link 18. Accordingly, the motor 50 and shaft define an axis of rotation for the finger link 20 about which the finger link can be rotated. In some embodiments, the motor 48 comprises a variable-assistance servomotor.

With further reference to FIG. 3, operation of the motor 48 is controlled by the motor controller 50, which is, in turn, controlled by the microcontroller 52. The microcontroller 52 sends commands to the motor controller 50 to open or close the gripper mechanism 16 in response to signals received from a flex sensor 54. The flex sensor 54 is configured to detect flexion and extension of the user's wrist when the orthotic gripper 10 is worn. With reference to FIG. 2, this flex sensor 54 can be integrated into the support sleeve 12. As shown in that figure, the flex sensor 54 can, for example, be attached to the sleeve 12 (e.g., sewn between layers of material of the sleeve) at a location at which the sensor extends across the ventral (inner) side of the wrist. The flex sensor 54 can be configured as an elongated sensor whose longitudinal axis is generally perpendicular to the bending axis of the wrist such that the sensor can easily detect flexion and extension of the wrist. Although the flex sensor 54 is illustrated in FIG. 2 as being located on the ventral side of the wrist, it is noted that the sensor can alternatively be positioned on the dorsal (outer) side of the wrist, if desired, as either placement is suitable for the purpose of detecting movement of the wrist. In addition, the orthotic gripper 10 can include more than one flex sensor, either on the same side of the sleeve 12 or on opposite sides of it. As is further shown in FIG. 2, the flex sensor 54 can be electrically coupled to the actuation device 38, and the microcontroller 52, with a wire or cable 56, which can be integrated into the material of the sleeve 12.

In some embodiments, each of the components shown in FIG. 3 can be powered by an onboard power source integrated into the orthotic gripper 10, such as a battery (not shown).

As identified above, the orthotic gripper 10 can be used to assist the user in grasping objects with a whole-hand grip. To do this, the user first positions the gripper 10 on the wrist and hand in the manner illustrated in FIGS. 1 and 2. As described above, the top of the support sleeve 12 can be opened for this purpose to enable the user to drop his or her wrist and hand into the sleeve and insert the thumb through the thumb sheath 14, if provided. Once the wrist and hand have been positioned within the sleeve 12, the sleeve can be wrapped snugly around the wrist and hand and the sleeve can be secured using the closure 17. At this point, the user can activate the gripping mechanism 16 using the control button 42. When the user does this, the indicator light 44 can illuminate to indicate to the user that the mechanism 16 is ready for use in grasping objects.

To grasp an object, the user can close his or her hand around the object with the assistance of the gripping mechanism 16. To do this, the user simply flexes his or her wrist, so as to turn the hand in toward the body. Such flexure is detected by the flex sensor 54, which sends a signal to the microcontroller 52 to alert it of this condition. When this signal is received, the microcontroller 52 signals the motor controller 50 to close the gripping mechanism 16 by activating the motor 48. The motor, in turn, rotates its shaft in a direction that causes the finger link 20 to rotate in a closing direction in which the finger link is moved closer to the thumb portion 22 of the thumb link 18. Because each finger is tied to the finger link 20, this causes all of the user's fingers to move closer to the thumb so that the target object can be gripped using a whole-hand grip, as opposed to a grip using only the thumb and the index finger.

In embodiments in which the motor 48 is a variable-assistance motor, the gripping mechanism 16 can be programmed to provide lesser or greater assistance to the user, as needed. For example, if one user has little control over his hand, the mechanism 16 can be programmed to provide greater assistance through the application of greater torque by the motor 48. If another user has better control over her hand, the mechanism 16 can be programmed to provide less assistance through the application of less torque by the motor 48. This feature can also be useful in rehabilitation contexts in which the user's ability to control the hand may change (e.g., improve) over time.

In some embodiments, the user can deactivate the gripping mechanism 16 once a desired position (either an open or closed position) has been achieved so as to lock the mechanism in that position. In such a case, the user can grip an object, deactivate the gripping mechanism 16 by pressing the control button 42, and therefore continuously hold the object irrespective of flexion or extension of the wrist. When the user wishes to release the object, he or she can then reactivate the gripping mechanism 16 and extend the wrist to open the hand. In some cases, the degree or the speed with which the gripping mechanism 16 opens or closes depends upon the degree to which the user extends or flexes the wrist. In such a case, slight flexion of the wrist can cause the gripping mechanism 16 to close slightly and/or slowly, while greater flexion of the wrist can cause the gripping mechanism to close to a greater degree and/or more quickly.

In other embodiments, the gripping mechanism 16 is configured such that the finger link 20 rotates when the wrist is moved from an initial neutral position between the opposing states of wrist flexion and wrist extension. In such a case, the finger link 20 will rotate toward the thumb link 18 in a closing direction when the wrist is flexed from the initial neutral position. Once both the fingers and thumb fully engage the object, the user can halt further closing of the finger link 20 by returning the wrist to the neutral position. As long as this neutral position is maintained, the finger link 20 will remain in the closed position at which the user halted closing. If the user wishes to release the object, the user can then extend the wrist from the neutral position, which causes the finger link 20 to rotate in an opening direction in which the finger link is moved away from the thumb portion 22 of the thumb link 18. This causes the user's fingers to move away from the thumb so that the target object can be released. With this type of functionality, the user need not press the control button 42 to grip and release objects, thereby enabling single-handed operation.

It is noted that other forms of actuation of the gripping mechanism 16 are possible. In each case, however, closure of the gripping mechanism 16 is achieved through either absolute or relative wrist flexion and opening of the gripping mechanism is achieved through either absolute or relative wrist extension.

Figure 5:
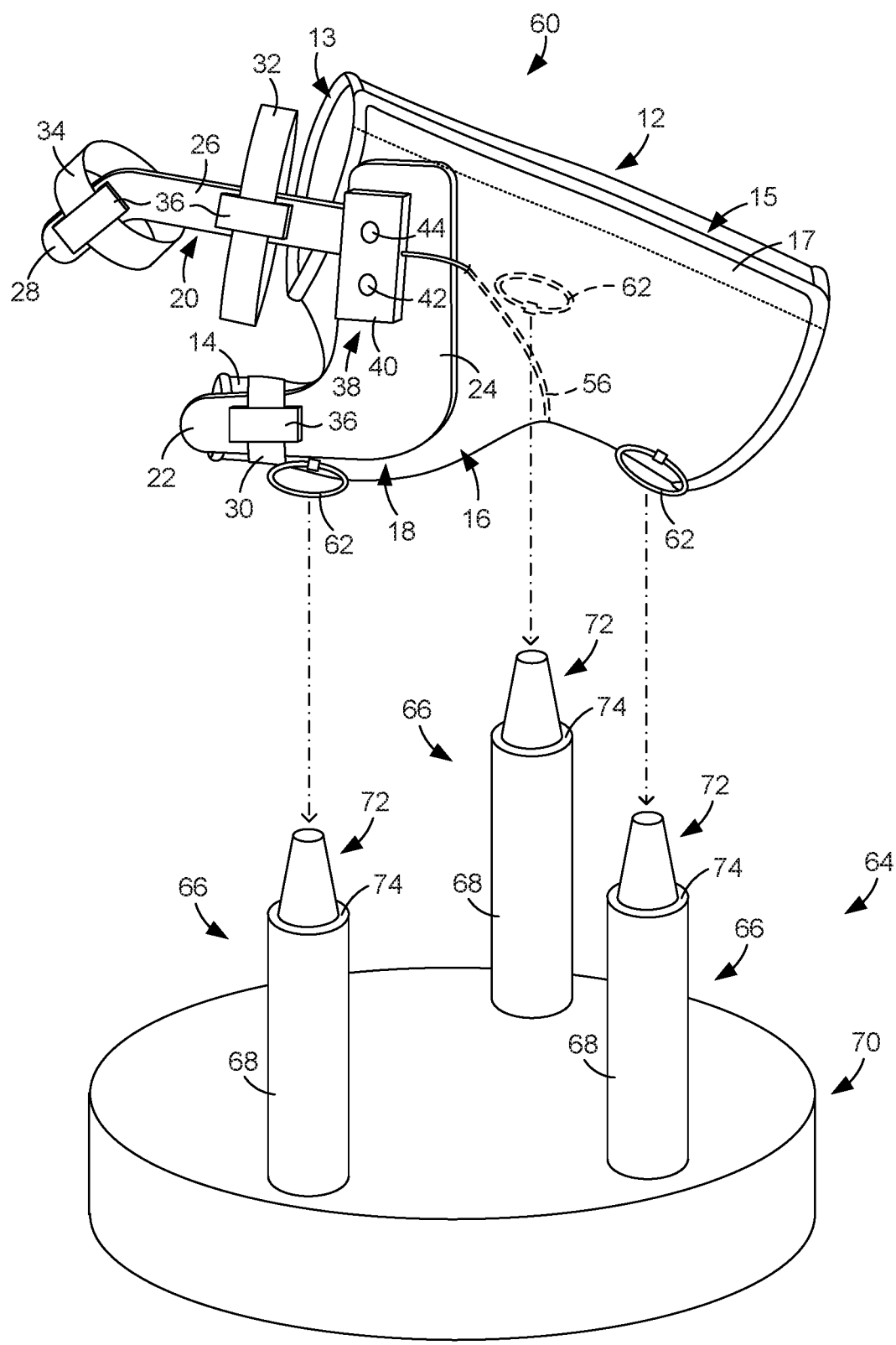
FIG. 5 is a perspective top view of a further embodiment of an orthotic gripper and a support stand that facilitates donning and doffing of the gripper.

FIG. 5 illustrates a further embodiment of an orthotic gripper 60. The gripper 60 is substantially identical to the gripper 10 shown in FIGS. 1 and 2 except that it further includes support rings 62 that are configured to assist the user in donning and doffing the gripper without the assistance of another person. In the illustrated embodiment, the gripper 60 includes three such rings, one attached to an inner lateral side of the support sleeve 12, one attached to an outer lateral side of the sleeve, and one attached to the thumb sheath 14. As depicted in FIG. 5, the gripper 60 can be lowered onto a support stand 64 in a manner in which each ring 62 passes over a support post 66 of the stand. Each post 66 can comprise an elongated shaft 68 that extends up from a base 70 of the stand 64. Positioned on the top end of each shaft 68 is a pointed tip 72 that makes it easier to pass a ring 62 onto the post 66. Surrounding the base of the tip 72 is a circular, horizontal seat 74 that is sized and configured to receive the ring 62 so that it is supported (seated) on the seat. Accordingly, the gripper 60 can be lowered onto the stand 64 such that each ring 62 rests upon a seat 74 of a post 66. When this is achieved, the gripper 60 is suspended by the rings 62 and, therefore, does not need to be held with the user's other hand when the gripper 60 is donned. When suspended by the stand 64, the top of the support sleeve 12 can be opened, the wrist and hand can be positioned within the sleeve in the appropriate manner (e.g., with assistance of the user's other hand), and the sleeve can be secured about the wrist and hand using the closure 17. The user can then lift the gripper 60 off of the stand 64 and use the gripper in the manner described above.

The locations of various components of the disclosed orthotic grippers have been described in relation to specific parts of the body. It is noted that these descriptions are intended to assist the user in understanding the locations of the components on or within the orthotic gripper. Accordingly, when a given component is described as being located near a particular part of the body, it will be understood that the component is positioned on or within the orthotic gripper in a location at which the component will be located near that body part when the orthotic gripper is properly worn by the user.

The invention claimed is:

1. An orthotic gripper comprising:
a support sleeve configured to wrap around a user's wrist and hand, the support sleeve including a top side configured to cover an outer side of the user's wrist and a bottom side configured to cover an inner side of the user's wrist;
a flex sensor mounted to the top side or the bottom side of the support sleeve, the flex sensor being configured to detect flexion and extension of the user's wrist; and
a gripping mechanism mounted to the support sleeve comprising a rigid thumb link configured to attach to a thumb of the user and a rigid finger link pivotally connected to the thumb link and configured to attach to one or more fingers of the user, the gripping mechanism being configured to move the finger link toward the thumb link when the flex sensor detects flexion of the wrist and to move the finger link away from the thumb link when the flex sensor detects extension of the wrist.

2. The orthotic gripper of claim 1, wherein the support sleeve is generally tubular and configured to extend from a point proximal of the user's wrist to a point near knuckles of the user's fingers.

3. The orthotic gripper of claim 2, wherein the support sleeve includes an opening at its distal end through which the user's finger can pass and a thumb sheath configured to wrap around the user's thumb.

4. The orthotic gripper of claim 3, wherein the support sleeve is elastic so as to be configured to snuggly wrap around the wrist and hand.

5. The orthotic gripper of claim 3, wherein the support sleeve includes a seam that extends along its length that can be opened to enable the user to drop the wrist and hand into the sleeve.

6. The orthotic gripper of claim 5, further comprising closure means associated with the seam configured to secure the sleeve in place around the wrist and hand.

7. The orthotic gripper of claim 1, further comprising a thumb strap attached to the thumb link and configured to wrap around the user's thumb and a finger strap attached to the finger link and configured to wrap around each of the user's fingers.

8. The orthotic gripper of claim 1, further comprising a motor mounted to the thumb link, wherein the motor comprises a shaft to which the finger link is mounted.

9. The orthotic gripper of claim 8, wherein the motor comprises a variable-assistance servomotor.

10. The orthotic gripper of claim 8, further comprising a microcontroller configured to receive signals from the flex sensor and control operation of the motor.

11. The orthotic gripper of claim 1, further comprising a control button configured to activate and deactivate the gripping mechanism.

12. The orthotic gripper of claim 11, further comprising an indicator light configured to indicate a state of operation of the gripping mechanism to the user.

13. The orthotic gripper of claim 1, further comprising support rings attached to the support sleeve that are configured to support the orthotic gripper in a suspended state so as to facilitate donning of the gripper.

14. An orthotic gripper configured to assist a user with gripping an object, the gripper comprising:
   an elastic support sleeve configured to wrap around a wrist and hand of the user, the sleeve being generally tubular and configured to extend from a point proximal of the user's wrist to a point near knuckles of fingers of the user, the sleeve including an opening at its distal end through which the user's fingers can pass and a thumb sheath configured to wrap around a thumb of the user, the sleeve including a top side configured to cover an outer side of the user's wrist and a bottom side configured to cover an inner side of the user's wrist;
   a flex sensor mounted to the top side or the bottom side of the sleeve and configured to detect flexion and extension of the wrist of the user; and
   a gripping mechanism mounted to the sleeve, the gripping mechanism comprising a rigid thumb link attached to the sleeve, the thumb link including a flexible thumb strap configured to wrap around the user's thumb, the gripping mechanism further comprising a rigid finger link pivotally connected to the thumb link, the finger link including a flexible finger strap configured to wrap around all of the user's fingers, the gripping mechanism further comprising a motor mounted on the thumb link and including a shaft to which the finger link is mounted, the gripping mechanism further comprising a microcontroller configured to receive signals from the flex sensor and control the motor in response to the received signals, wherein the microcontroller is configured to rotate the finger link toward the thumb link with the motor when the flex sensor detects flexion of the wrist and to rotate the finger link away from the thumb link with the motor when the flex sensor detects extension of the wrist.

15. A method for assisting a user in grasping an object, the method comprising: attaching a flex sensor to a wrist of a user and a gripping mechanism to a hand of the user, the gripping mechanism including a thumb link configured to attach to a thumb of the user and a finger link configured to attach to fingers of the user; sensing flexion and extension of the wrist with the flex sensor; and opening or closing the gripping mechanism responsive to the flex sensor detecting flexion or extension of the wrist, the gripping mechanism being configured to move the finger link toward the thumb link when the flex sensor detects flexion of the wrist and to move the finger link away from the thumb link when the flex sensor detects extension of the wrist.

16. The method of claim 15, wherein the flex sensor and the gripping mechanism are mounted to a support sleeve and wherein attaching the flex sensor to the wrist of the user and the gripping mechanism to the hand of the user comprises attaching the sleeve to the user's wrist and hand.

17. The method of claim 16, wherein attaching the gripping mechanism to the hand further comprises wrapping a thumb strap of the thumb link around a thumb of the user and wrapping a finger sleeve of the finger link around the fingers of the user.

* * * * *